(12) United States Patent
Coates et al.

(10) Patent No.: US 7,569,709 B2
(45) Date of Patent: Aug. 4, 2009

(54) LOW PRESSURE CARBONYLATION OF HETEROCYCLES

(75) Inventors: Geoffrey W. Coates, Ithaca, NY (US); John Kramer, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/705,528

(22) Filed: Feb. 13, 2007

(65) Prior Publication Data

US 2007/0213524 A1    Sep. 13, 2007

Related U.S. Application Data

(60) Provisional application No. 60/780,884, filed on Mar. 10, 2006.

(51) Int. Cl.
*C07D 305/00* (2006.01)
*C07D 303/00* (2006.01)
(52) U.S. Cl. .................. 549/510; 549/512; 549/513
(58) Field of Classification Search ............ 549/510, 549/512, 513
See application file for complete search history.

(56) References Cited

U.S. PATENT DOCUMENTS 6,852,865 B2 * 2/2005 Coates et al. ............ 548/950

OTHER PUBLICATIONS

Getzier et al. Journal of the American Chemical Society, 2004, 126, 6842-6843.*
Kramer, John W., et al., "Practical β-Lactone Synthesis: Epoxide Carbonylation at 1 atm", Organic Letters, vol. 8, No. 17, 2006, pp. 3709-3712.

* cited by examiner

*Primary Examiner*—D. Margaret Seaman
*Assistant Examiner*—Nizal S Chandrakumar
(74) *Attorney, Agent, or Firm*—Charles E. Lyon; Choate, Hall & Stewart, LLP

(57) ABSTRACT

Heterocycles, e.g., epoxides, are carbonylated at low pressure with high percentage conversion to cyclic, ring expanded products using the catalyst

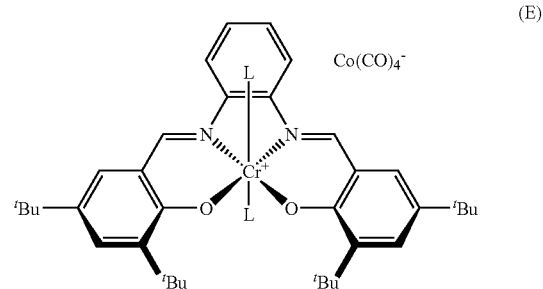

where L is tetrahydrofuran (THF).

27 Claims, No Drawings

LOW PRESSURE CARBONYLATION OF HETEROCYCLES

CROSS-REFERENCES TO RELATED APPLICATIONS

This application claims the benefit of U.S. Provisional Patent Application No. 60/780,884, filed Mar. 10, 2006, the whole of which is incorporated herein by reference.

This invention was made at least in part with U.S. Government support under National Science Foundation Grant No. CHE-0243605 and Department of Energy Grant No. DE-FG02-05ER15687 and the National Institutes of Health Chemical Biology Interface (CBI) Training Grant. The U.S. Government has certain rights in the invention.

FIELD OF THE INVENTION

The invention is directed to catalytic carbonylation of epoxides, aziridines, thiiranes, oxetanes, lactones, lactams and analogous compounds.

BACKGROUND OF THE INVENTION

U.S. Pat. No. 6,852,865 is directed to carbonylation of epoxides, aziridines, thiiranes, oxetanes, lactones, lactams and analogous compounds in the presence of a catalytically effective amount of catalyst having the general formula [Lewis acid]$^{z+}$ {[QM(CO)$_x$]$^{w-}$}$_y$ where Q is any ligand and need not be present, M is a transition metal selected from the group consisting of Groups 4, 5, 6, 7, 8, 9 and 10 of the periodic table of elements, z is the valence of the Lewis acid and ranges from 1 to 6, w is the charge of the metal carbonyl and ranges from 1 to 4 and y is a number such that w times y equals z, and x is a number such as to provide a stable anionic metal carbonyl for {[QM(CO)$_x$]$^{w-}$}$_y$ and ranges from 1 to 9 and typically from 1 to 4. CO pressures ranging from 100 to 1000 psig are disclosed. High percentage conversions were obtained at CO pressures of 800 psig and 900 psig; these pressures require the use of a high pressure reactor.

SUMMARY OF THE INVENTION

It has been found herein that high percentage conversions can be obtained with low CO pressures when a particular catalyst (A) as described below is utilized.

The invention herein is directed to carbonylation of a compound having the formula:

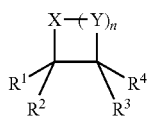

(I)

where R$^1$, R$^2$, R$^3$ and R$^4$ are the same or different and are each selected from the group consisting of a hydrogen atom, a halogen atom, a carbon-containing group, a fluorine containing group, a heterocyclic compound residue, an oxygen-containing group, a nitrogen-containing group, a boron-containing group, a sulfur-containing group, a phosphorus-containing group, a silicon-containing group, and two or more of these can be bonded to each other to form a ring or rings, and X is selected from the group consisting of O, S and NR$^5$, where R$^5$ is selected from the group consisting of a hydrogen atom, a halogen atom, a carbon-containing group, a fluorine-containing group, a heterocyclic compound residue, an oxygen-containing group, a nitrogen-containing group, a boron-containing group, a sulfur-containing group, a phosphorus-containing group, and a silicon-containing group, and where n is 0 or 1, and Y is C=O or CH$_2$, said process comprising the step of reacting compound (I) with carbon monoxide under a pressure enabling reaction in glassware, e.g., a pressure ranging from ambient pressure (e.g., 1 atmosphere) to 125 psig, in the presence of a catalytically effective amount of a catalyst (A), described below, to form a product having the structural formula:

(II)

where R$^1$, R$^2$, R$^3$ and R$^4$ and X correspond to R$^1$, R$^2$, R$^3$ and R$^4$ and X in (I) including two or more of R$^1$, R$^2$, R$^3$ and R$^4$ forming a ring if that is the case for (I); and in the case where n for (I) is 0, n for (II) is 0, 1 or 2, and in the case where n for (I) is 1, n for (II) is 1 or 2.

R$^1$, R$^2$, R$^3$, R$^4$ and R$^5$ can also be any other functionality that the catalyst referred to below is tolerant of. The term "any other functionality that the catalyst referred to below is tolerant of" is used herein to mean that the functionality can be present without causing the catalyst to be inactive.

The catalyst (A) has the formula:

k[QM'(CO)$_y$]$^{z-}$[M(JR$_q$)$_m$]$^{p+}$  (A)

where k is an integer ranging from 1 to 6, Q can be present or absent and is any ligand bound to M' and if present, is selected from the group consisting of a phosphine group, phosphite, group comprising pyridine moiety, C$_1$-C$_{30}$ alkyl, C$_6$-C$_{30}$ aryl, C$_1$-C$_{30}$ acyl, and carbene, such that a stable metal complex is formed, M' is a metal from groups 4-10 of the periodic table, y is an integer ranging from 0 to 6, z is the charge on the anionic portion and ranges from 1 to 4, M is selected from the group consisting of a metal atom from groups 2-15 of the periodic table, lanthanides and actinides, J is selected from the group consisting of a hydrogen atom, a halogen atom, a carbon atom, a nitrogen atom, a sulfur atom, a phosphorus atom, and an oxygen atom, R is optionally present and, if present, is a hydrogen atom or a carbon-containing group containing 1 to 30 carbon atoms, q is an integer ranging from 0 to 3, m is an integer ranging from 0 to 6 and p is the charge on the cationic portion and is equal to the product of k and z.

The catalyst of these denoted (E), found to be best, has the structural formula.

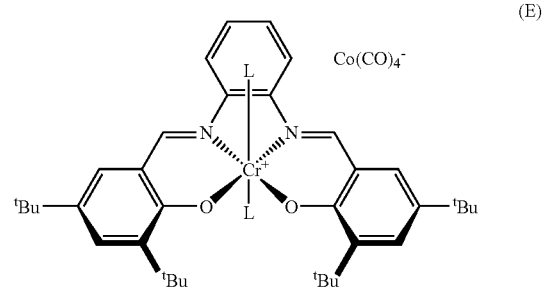

(E)

where L is tetrahydrofuran (THF).

The reaction is preferably carried out in glassware. As used herein "glassware" means, for example, a glass reactor, for example, a Fisher Porter bottle, at 100 psig, or a round bottom glass flask, a glass vial or other glass vessel that can hold 1 atmosphere of CO.

As used herein the term "halogen atom" includes, for example, a chlorine atom, a fluorine atom, an iodine atom, or a bromine atom.

As used herein the term "high percentage conversion" means at least 40% conversion. The percent conversion to (II) is preferably 90% or more, very preferably 95% or more.

A second embodiment herein is directed to carbonylation of a compound having the structure (I) as defined for the first embodiment, comprising reacting Compound (I) with carbon monoxide in a reactor that does not comprise stainless steel. The advantage of this is that nickel and iron are present in stainless steel and nickel and iron carbonyls formed during carbonylation inside a reactor are highly toxic.

DETAILED DESCRIPTION

We turn now to further description of $R^1$, $R^2$, $R^3$, $R^4$ and $R^5$ for (I) and (II). The carbon containing group can be, for example, $C_1$-$C_{100,000}$ alkyl, $C_2$-$C_{100,000}$ alkenyl and $C_6$-$C_{100,000}$-aryl, or alkaryl containing from 1 to 20 carbon atoms; these are optionally substituted, for example, with halogen (including, for example, substitution of fluorine atom on one or more carbons and/or substitution of one or more trifluorocarbon groups) or with benzyl ether. The oxygen-containing group can be, for example, ester-containing moiety containing from 1 to 20 carbon atoms, ketone containing moiety containing from 1 to 20 carbon atoms, alcohol containing moiety containing from 1 to 20 carbon atoms, an acid containing moiety containing 1 to 20 carbon atoms, or an aldehyde containing moiety containing 1 to 20 carbon atoms and can be an ether containing moiety where the ether group contains from 1 to 20 carbon atoms and can be oxygen-containing (in addition to the ether oxygen) or can be a benzyl ether or can be a glycidyl ester where the ester group can be $C_1$-$C_{20}$ alkyl, $C_2$-$C_{20}$ alkenyl, $C_6$-$C_{20}$ aryl or $C_6$-$C_{20}$ arylalkyl. The nitrogen-containing group, can contain, for example, from 1 to 20 carbon atoms and contain an amide moiety. The sulfur-containing group can contain, for example, 1 to 20 carbon atoms and can be or contain tosyl group or contain tosyl moiety or be or contain a sulfonate group. The silicon-containing group can be, for example, alkyl substituted silyl ether where the ether group is $C_1$-$C_6$ alkylene and alkyl substitution consists of one to three $C_1$-$C_6$ alkyl, substituted on silyl.

In one case, n for (I) is 0 so that the structural formula for (I) becomes:

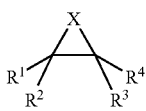

and the product has the structural formula:

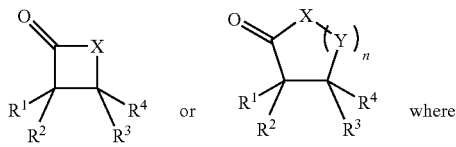

n is 1 and Y is C=O.

In a subset (a) of this case carried out at CO pressure of 100 psig (6.8 atm), the reaction equation is:

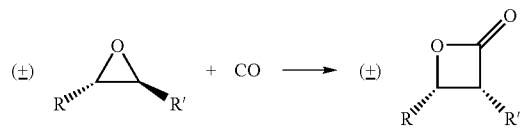

where R is the same as $R^3$ above and R' is the same as $R^1$ above.

In a subset (b) of this case carried out at CO pressure of 1 atmosphere (0 psig), the reaction equation is:

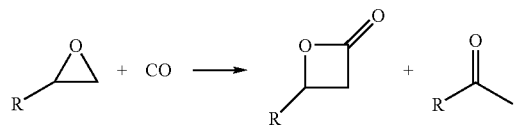

where R is the same as $R^3$ above.

The subset (a), that is the 100 psig CO pressure case, requires special glassware, e.g., a Fisher-Porter bottle, but gives essentially no side products. The special glassware is much less expensive than the high pressure reactor used in examples in U.S. Pat. No. 6,852,865.

The subset (b), that is the 1 atm CO pressure case, can use a glass roundbottom flask or other glassware, for example, a glass vial or other glass vessel that can hold 1 atmosphere of CO, but results in some side products as indicated in Kramer, J. W., et al., Org. Lett. 8(17), 3709-3712 (Jul. 18, 2006), the whole of which is incorporated herein by reference.

We turn now to the catalysts.

A preferred catalyst (A) is catalyst (B) which has the structural formula:

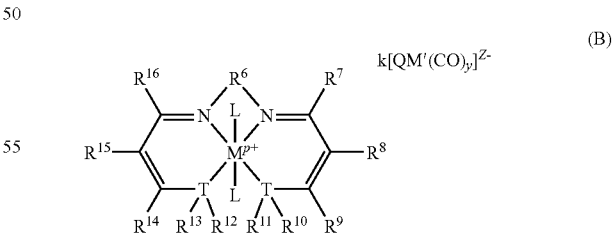

where M, p and $k[QM'(CO)_y]^{z-}$ are the same as for (A), each T can be the same or different and is selected from the group consisting of a sulfur atom, an oxygen atom, a nitrogen atom or a phosphorus atom; $R^{12}$, $R^{13}$, $R^{10}$ and $R^{11}$ are optional and are each selected form the group consisting of a hydrogen atom, a halogen atom, a carbon-containing group containing 1 to 30 carbon atoms, a heterocyclic compound residue, an oxygen-containing group, nitrogen-containing group, a boron-containing group, a sulfur-containing group, a phosphorus-containing group, a silicon-containing group, and two or more of them can be bonded to each other to form a ring or rings; and $R^{14}$, $R^{15}$, $R^{16}$, $R^6$, $R^7$, $R^8$ and $R^9$ are each a hydrogen atom, a carbon-containing group containing 1-30 carbon atoms, a heterocyclic compound residue, an oxygen-containing group, a nitrogen-containing group, a boron-containing group, a sulfur-containing group, a phosphorus-containing group, or a silicon-containing group, except that $R^6$ is not a hydrogen atom and two or more of them and $R^{10}$, $R^{11}$ and $R^{12}$ and $R^{13}$ can be bonded to each other to form a ring or rings; and L is a Lewis base, which can be absent, and if present, each L is the same or different and is selected from the group consisting of ethers (e.g., tetrahydrofuran), thioethers, esters, amines, pyridines, phosphines, phosphites, nitriles and carbenes.

A preferred catalyst (B) is catalyst (C), which has the structural formula:

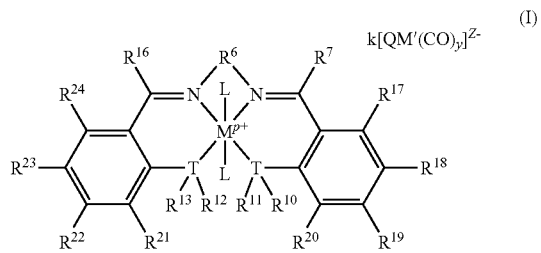

where M, T, p, $k[QM'(CO)_y]^{z-}$, $R^{12}$, $R^{13}$, $R^{10}$, $R^{11}$, $R^{16}$, $R^6$, $R^7$ and L are the same as for (B), and $R^{21}$, $R^{22}$, $R^{23}$, $R^{24}$, $R^{17}$, $R^{18}$, $R^{19}$ and $R^{20}$ are the same or different and are each selected from the group consisting of a hydrogen atom, a halogen atom, a carbon-containing group containing from 1 to 30 carbon atoms, a heterocyclic compound residue, an oxygen-containing group, a nitrogen-containing group, a boron-containing group, a sulfur-containing group, a phosphorus-containing group, a silicon-containing group, and two or more of them and $R^6$, $R^7$, $R^{10}$, $R^{11}$, $R^{12}$, $R^{13}$ and $R^{16}$ can be bonded to each other to form a ring or rings.

A preferred catalyst (C) is catalyst (D) which has the structural formula:

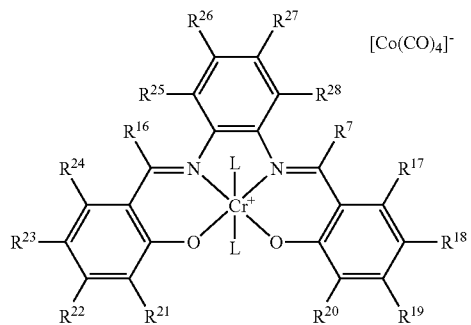

where $R^{16}$, $R^7$, $R^{21}$, $R^{22}$, $R^{23}$, $R^{24}$, $R^{17}$, $R^{18}$, $R^{19}$, $R^{20}$ and L are the same as for (C) and $R^{25}$, $R^{26}$, $R^{27}$ and $R^{28}$ are the same or different and are selected from the group consisting of a hydrogen atom, a halogen atom, a carbon-containing group containing 1 to 30 carbon atoms, a heterocyclic compound residue, an oxygen-containing group, a nitrogen-containing group, a boron-containing group, a sulfur-containing group, a phosphorus-containing group, a silicon-containing group, and two or more of them and $R^{16}$, $R^7$, $R^{21}$, $R^{22}$, $R^{23}$, $R^{24}$, $R^{17}$, $R^{18}$, $R^{19}$ and $R^{20}$ can be bonded to each other to form a ring or rings.

Catalyst G1 described in U.S. Pat. No. 6,852,865, that is $[Cp_2Ti(THF)_2][Co(CO)_4]$ where Cp means cyclopentadienyl has been found not to work at all for epoxide carbonylation carried out at CO pressures of 100 psig and below and is excepted from the catalysts herein.

The catalyst (A) herein can be made by reaction of $M(JR_q)$ X' where $M(JR_q)$ is defined as for catalyst (A) with QM'$(CO)_y$—Y' where QM'$(CO)_y$ is defined as for catalyst (A) and X' is any leaving group and Y' is a moiety that will form a salt with X'.

We turn now to the catalyst (E). It is readily made as described in Supporting Information for Kramer, J. W., et al., Org. Lett. 8(17), 3709-3712 (Jul. 18, 2006), the whole of which is incorporated herein by reference.

We turn now to the reaction conditions besides starting material, CO pressure and catalyst.

The mole ratio of component (I) charged to catalyst charged, can range, for example, from 1:1 to 10,000:1, for example, from 25:1 to 150:1. For subset (a), the mole ratio used in the examples was 100:1, for subset (b), the mole ratio used in the examples was 50:1.

Where the CO pressure is greater than 1 atm, e.g., when it is 100 psig, the pressure and the volume of the reactor define the amount of CO. Where the CO pressure is one atmosphere, the amount of CO is provided by the headspace in the reactor which is, for example, 200 to 1000 ml.

The solvent for the reaction used in experiments herein was dimethoxyethane (DME). Other useful solvents include diglyme, triglyme, tetrahydrofuran and toluene. The reaction may be carried out in any solvent in which the starting material and catalyst are at least partially soluble.

The reaction can be carried out at room temperature.

The time of reaction can range, for example, from 1 minute to 50 hours or even longer. The reactions of subset (a) obtained clean carbonylation to the corresponding beta-lactone within three hours. The reactions of subset (b) were carried out for 6 hours.

Elements of the invention and working examples are set forth in Kramer, J. W., Lobkovsky, E. B., and Coates, G. W., Org. Lett. 8(17), 3709-3712 (Jul. 18, 2006), the whole of which is incorporated herein by reference.

We turn now to the second embodiment herein.

It has been documented that stainless steel and CO produce $Fe(CO)_5$ and $Ni(CO)_4$ (See Shriver, D., et al., Inorganic Chemistry, W. Friedman and Co., 1990, page 508) which are both very toxic. Carbonylation reactions run in other types of reactors do not have this problem. These other reactors can comprise as material of construction, for example, glass, plastic, aluminum or brass. The glass reactors can be, for example, a Fisher Porter bottle, for reaction at 100 psi, or a round bottom glass flask or glass vial or other glass vessel that can hold 1 atm of CO for reactions at 1 atm.

The invention is illustrated in the following working examples.

CARBONYLATION EXAMPLE I

Epoxide carbonylation was carried out with 100 psig CO using catalyst E, according to the process of subset (a) described above. As indicated above, the reaction equation for subset (a) is where R is the same as $R^3$ above and R' is the same as $R^1$ above. Conditions and results are set forth in Table 1 below.

TABLE 1

| Entry | R | R' | t[h] | Conv.[b][%] |
|---|---|---|---|---|
| 1 | Me | H | 2 | 99 |
| 2 | Et | H | 1 | 99 |
| 3 | $(CH_2)_9CH_3$ | H | 2 | 99 |
| 4 | $(CH_2)_2CH=CH_2$ | H | 2 | 99 |
| 5 | $CH_2OCH_2CH=CH_2$ | H | 1 | 99 |
| 6 | $CH_2O^nBu$ | H | 1 | 99 (88)[c] |
| 7 | $CH_2OSiMe_2{}^tBu$ | H | 1 | 99 |
| 8 | $CH_2OC(O)CH_3$ | H | 2 | 99 |
| 9 | $CH_2OC(O)Ph$ | H | 3 | 99 |
| 10 | $CH_2Cl$ | H | 3 | 99 |
| 11[d] | Me | Me | 8 | 99[e] |

[a] All reactions were stirred in a Fisher-Porter bottle using 2 mmol epoxide in 2 mL DME and 1 mol % at RT, unless noted otherwise
[b]Conversion determined by $^1$H NMR spectroscopy (and confirmed by GC for entry 1); β-lactone was exclusive product.
[c]Isolated yield from one-gram scale reaction.
[d]2 mol % 1.
[e] Product was cis-3,4-dimethyl-2-propiolactone.

CARBONYLATION EXAMPLE II

Epoxide carbonylation was carried out with 1 atmosphere CO, according to the process of subset (b) described above. As indicated above, the reaction equation for subset (b) is

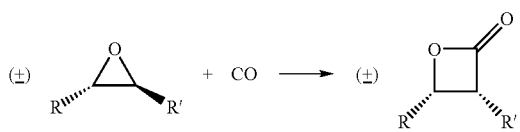

where R is the same as $R^3$ above.

Conditions and results are set forth in Table 2 below.

TABLE 2

| Entry | R | Conv.[b] [%] | β-Lactone:Ketone[b] |
|---|---|---|---|
| 1 | Me | 99 | 96:4 |
| 2 | Et | 99 | 97:3 |
| 3 | $(CH_2)_9CH_3$ | 99 | 99:1 |
| 4 | $(CH_2)_2CH=CH_2$ | 99 | 95:5 |
| 5 | $CH_2OCH_2CH=CH_2$ | 99 | 93:7 |
| 6 | $CH_2O^nBu$ | 99 | 89:11 |
| 7 | $CH_2OSiMe_2{}^tBu$ | 99 | 96:4 |
| 8 | $CH_2OC(O)CH_3$ | 99 | 95:5 |
| 9 | $CH_2OC(O)Ph$ | 89[c] | 95:5 |
| 10 | $CH_2Cl$ | 35[c] | 89:11 | a] Carbonylation reactions performed in a CO-filled, 500-mL round-bottom flask with 2 mmol epoxide, 2 mL DME, and 2 mol % 1 stirred at RT for six hours
[b]Conversion and product ratios determined by $^1$H NMR spectroscopy
[c]Remainder was unreacted epoxide

CARBONYLATION EXAMPLE III

Epoxide carbonylation was carried out using Catalyst E at 100 psi CO according to the procedure of Carbonylation Example I except using epoxide and reaction time and providing lactone product and yield percent as set forth in Table 3 below.

TABLE 3

| Entry | Epoxide | Time (h) | Yield (%) | Lactone |
|---|---|---|---|---|
| 12 | (cyclohexyl epoxide) | 2.5 | 99 | (cyclohexyl β-lactone) |
| 13 | Ph-O-CH₂CH₂-(epoxide) | 1.5 | 99 | Ph-O-CH₂CH₂-(β-lactone) |
| 14 | Ph-O-(CH₂)₄-(epoxide) | 20 | 99 | Ph-O-(CH₂)₄-(β-lactone) |

| | | |
|---|---|---|
| 15 | 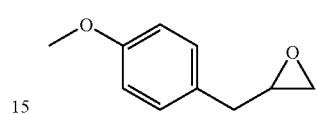 | 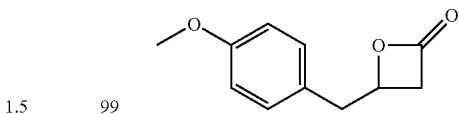 1.5  99 |
| 16 | 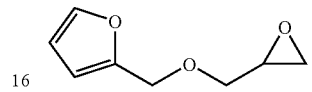 | 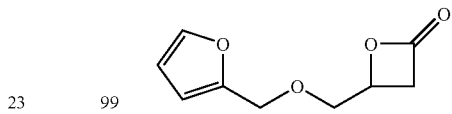 23  99 |
| 17 | 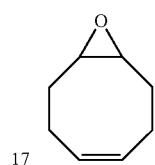 | 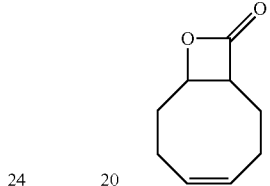 24  20 |
| 18 | 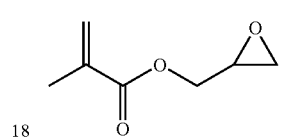 | 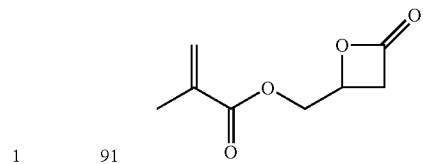 1  91 |
| 19 | 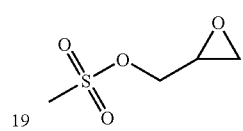 | 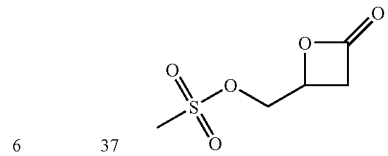 6  37 |
| 20 | 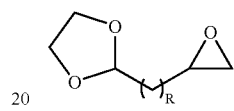 | 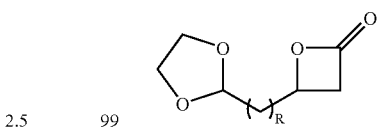 2.5  99 |
| 21 | 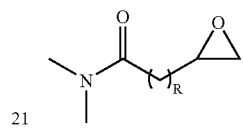 | 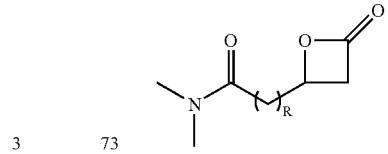 3  73 |
| 22 | 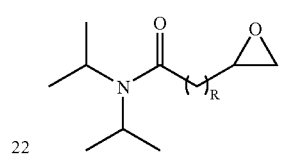 | 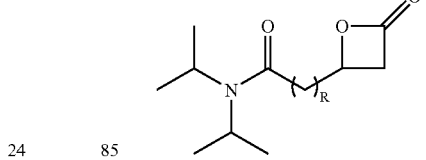 24  85 |
| 23 | 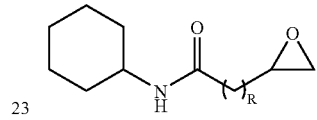 | 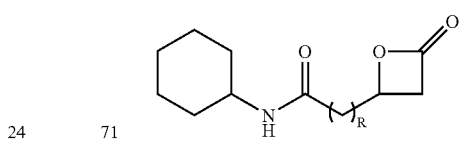 24  71 |
| 24 | 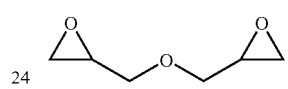 | 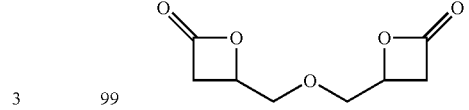 3  99 |

| 11 | | 12 |
|---|---|---|
| 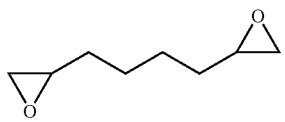 | | 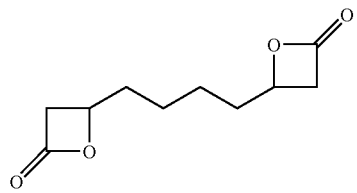 |
| 25 | 2 | 99 |
| 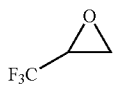 | | 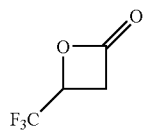 |
| 26 | 48 | 87 |
| 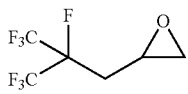 | | 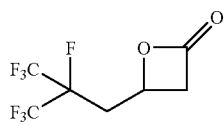 |
| 27 | 16 | 99 |
| 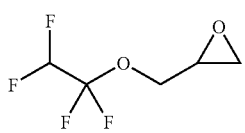 | | 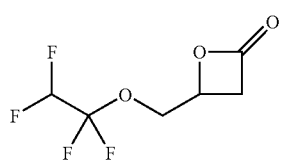 |
| 28 | 3 | 99 |
| 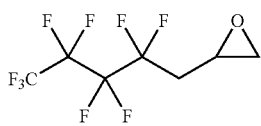 | | 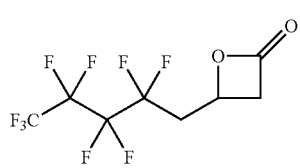 |
| 29 | 24 | 99 |
| | | 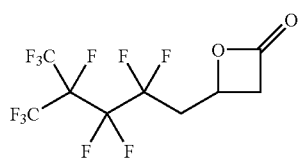 |
| 30 | 19 | 99 |
| | | 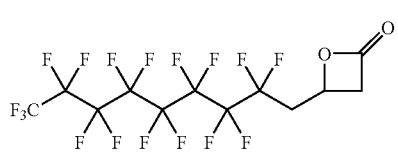 |
| 31 | 15 | 99 |

Variations

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A process for carbonylation of a compound having the formula:

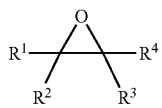

(I)

where $R^1$, $R^2$, $R^3$ and $R^4$ are the same or different and are each selected from the group consisting of a hydrogen atom, a halogen atom, a carbon-containing group, a fluorine containing group, a heterocyclic compound residue, an oxygen-containing group, a nitrogen-containing group, a boron-containing group, a sulfur-containing group, a phosphorus-containing group, a silicon-containing group, and two or more of these can be bonded to each other to form a ring or rings;

said process comprising the steps of reacting compound (I) with carbon monoxide under a pressure up to 125 psi, in the presence of a catalytically effective amount of a catalyst (D), described below, to yield a beta-lactone where the catalyst (D) has the formula:

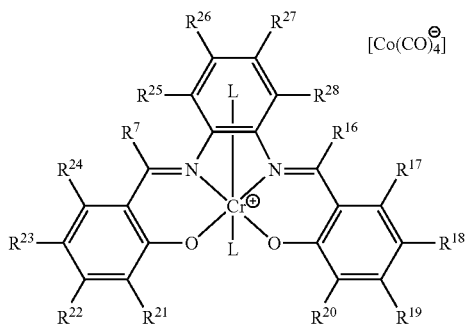

where $R^7$ and $R^{16}$ are each a hydrogen atom, a carbon-containing group containing 1-30 carbon atoms, a heterocyclic compound residue, an oxygen-containing group, a nitrogen-containing group, a boron-containing group, a sulfur-containing group, a phosphorus-containing group, or a silicon-containing group;

where $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are the same or different and are selected from the group consisting of a hydrogen atom, a halogen atom, a carbon-containing group containing 1 to 30 carbon atoms, a heterocyclic compound residue, an oxygen-containing group, a nitrogen-containing group, a boron-containing group, a sulfur-containing group, a phosphorus-containing group, a silicon-containing group, and two or more of $R^7$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ can be bonded to each other to form a ring or rings; and where L is a Lewis base, which can be absent, and if present, each L is the same or different and is selected from the group consisting of ethers, thioethers, esters, amines, pyridines, phosphines, phosphites, nitriles and carbenes.

2. The process of claim 1 were the catalyst (D) has the structural formula:

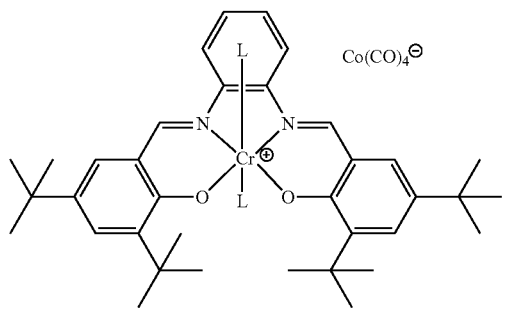

where L is tetrahydrofuran.

3. The process of claim 2 where the reaction is carried out in glassware.

4. The process of claim 2 where the carbon monoxide is at a pressure of 100 psig.

5. The process of claim 2 where the reaction is carried out at atmospheric pressure.

6. The process of claim 1 where $R^1$, $R^2$, $R^3$ and $R^4$ are the same or different and are each selected from the group consisting of a hydrogen atom and a carbon-containing group with from 1 to 20 carbons.

7. The process of claim 1 where $R^1$, $R^2$, $R^3$ and $R^4$ are the same or different and are each selected from the group consisting of a hydrogen atom and an oxygen-containing group with from 1 to 20 carbons.

8. The process of claim 1 where $R^1$, $R^2$, $R^3$ and $R^4$ are the same or different and are each selected from the group consisting of a hydrogen atom and a nitrogen-containing group with from 1 to 20 carbons.

9. The process of claim 1 where $R^1$, $R^2$, $R^3$ and $R^4$ are the same or different and are each selected from the group consisting of a hydrogen atom and a sulfur-containing group with from 1 to 20 carbons.

10. The process of claim 1 where $R^2$ and $R^4$ are hydrogen atoms.

11. The process of claim 10 where $R^1$ and $R^3$ are methyl.

12. The process of claim 1 where $R^2$, $R^3$ and $R^4$ are hydrogen atoms.

13. The process of claim 12 where $R^1$ is selected form the group consisting of:

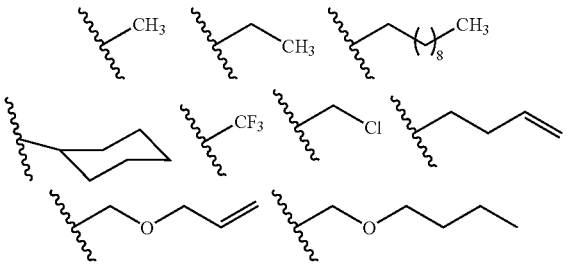

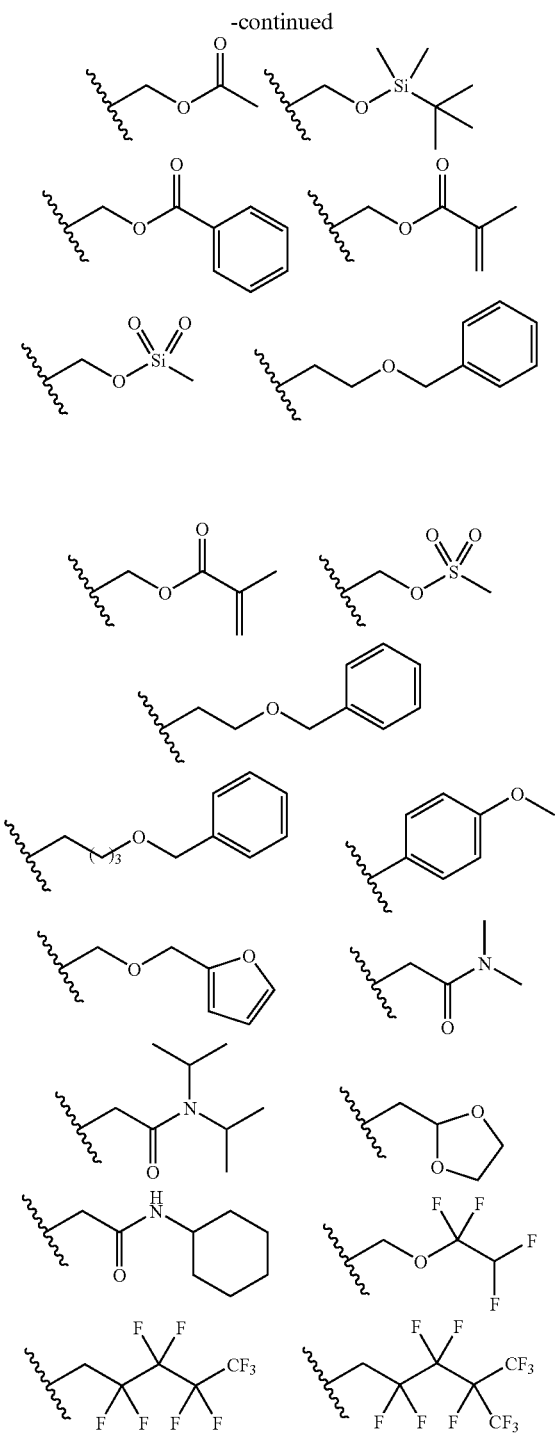

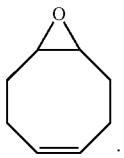

14. The process of claim 1 where $R^1$, $R^2$, $R^3$ and $R^4$ are each hydrogen and the product is propiolactone.

15. The process of claim 1 where $R^1$ is methyl, $R^2$, $R^3$ and $R^4$ are each hydrogen and the product is beta-butyrolactone.

16. The process of claim 1 where $R^2$ and $R^4$ are hydrogen and $R^1$ and $R^3$ taken together with the atoms to which they are attached form a ring.

17. The process of claim 16 where (I) is cyclohexene oxide.

18. The process of claim 16 where (I) is

19. The process of claim 1 where $R^7$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are each a hydrogen atom or a carbon-containing group containing 1-30 carbon atoms.

20. The process of claim 1 where at least one L is tetrahydrofuran.

21. The process of claim 1 where the reaction is carried out in glassware.

22. The process of claim 1 where the carbon monoxide is at 100 psig.

23. The process of claim 1 where the reaction is carried out at atmospheric pressure.

24. The process of claim 1 where the mole ratio of (I) charged into the reaction to catalyst (D) charged is in the range of 1:1 to 10,000:1.

25. The process of claim 1 where the mole ratio of (I) charged into the reaction to catalyst (D) charged is in the range of 25:1 to 150:1.

26. The process of claim 1 where the reaction is carried out in a solvent selected from the group consisting of dimethoxyethane, diglyme, triglyme, tetrahydrofuran and toluene.

27. The process of claim 1 where the reaction is carried out in dimethoxyethane.

\* \* \* \* \*